(12) United States Patent
Hansen (10) Patent No.: US 9,545,296 B2
(45) Date of Patent: Jan. 17, 2017

(54) DIGITAL FACE BOW SYSTEM AND METHOD

(71) Applicant: Stephen R Hansen, Fircrest, WA (US)

(72) Inventor: Stephen R Hansen, Fircrest, WA (US)

(*) Notice: Subject to any disclaimer, the term of this patent is extended or adjusted under 35 U.S.C. 154(b) by 250 days.

(21) Appl. No.: 14/451,313

(22) Filed: Aug. 4, 2014

(65) Prior Publication Data

US 2016/0030144 A1    Feb. 4, 2016

Related U.S. Application Data

(60) Provisional application No. 61/862,281, filed on Aug. 5, 2013.

(51) Int. Cl.
  *A61C 9/00*    (2006.01)
  *A61C 19/045*  (2006.01)
  *A61C 11/08*   (2006.01)

(52) U.S. Cl.
  CPC ........... *A61C 19/045* (2013.01); *A61C 9/0006* (2013.01); *A61C 11/08* (2013.01)

(58) Field of Classification Search
  CPC ...... A61C 19/045; A61C 9/0006; A61C 11/08
  See application file for complete search history.

(56) References Cited

U.S. PATENT DOCUMENTS

| | | | |
|---|---|---|---|
| 4,734,034 A | 3/1988 | Maness et al. | |
| 4,856,993 A | 8/1989 | Maness et al. | |
| 5,278,756 A | 1/1994 | Lemchen et al. | |
| 5,739,431 A * | 4/1998 | Petri | E21B 47/02 324/260 |
| 5,752,832 A | 5/1998 | Vardimon et al. | |
| 5,954,647 A | 9/1999 | Bova et al. | |
| 6,099,314 A | 8/2000 | Kopelman et al. | |
| 6,364,660 B1 | 4/2002 | Durbin et al. | |
| 7,013,191 B2 | 3/2006 | Rubbert et al. | |
| 7,144,251 B1 | 12/2006 | Karapetyan | |
| 8,348,669 B1 | 1/2013 | Schmitt | |
| 2004/0167646 A1 | 8/2004 | Jelonek et al. | |
| 2005/0089822 A1 | 4/2005 | Geng | |
| 2005/0153257 A1 | 7/2005 | Durbin et al. | |
| 2005/0203726 A1 | 9/2005 | Marshall | |
| 2006/0079981 A1 | 4/2006 | Rubbert et al. | |
| 2006/0095242 A1 | 5/2006 | Marshall | |
| 2006/0160044 A1 | 7/2006 | Olivier | |
| 2006/0188839 A1 * | 8/2006 | Adams | A61C 19/05 433/68 |
| 2006/0210946 A1 | 9/2006 | Meulener | |
| 2007/0190481 A1 | 8/2007 | Schmitt | |

(Continued)

*Primary Examiner* — Robert N Wieland
(74) *Attorney, Agent, or Firm* — George A. Leone; Citadel Patent Law (57) ABSTRACT

A digital face bow system for capturing a patient's dento-facial characteristics by acquiring and registering data defining the tilt or slant of the occlusal or incisal plane of a patient's teeth in three planes of space in relation to the cranium, head and/or face. The system includes a substrate adapted to support bite registration material, and a digital multiple axis inclinometer coupled to the substrate for registering the orientation of the occlusal or incisal plane, where the midline of the patient's horizontal-facial plane is registered. An adjustable mounting platform is adapted to receive the substrate and replicate the inclination registered by the digital multiple axis inclinometer.

17 Claims, 7 Drawing Sheets

(56) References Cited

U.S. PATENT DOCUMENTS

| | | |
|---|---|---|
| 2007/0190492 A1 | 8/2007 | Schmitt |
| 2007/0254261 A1* | 11/2007 | Rosenblood ......... A61C 1/0015 433/98 |
| 2008/0085489 A1 | 4/2008 | Schmitt |
| 2009/0291417 A1 | 11/2009 | Rubbert et al. |
| 2010/0067756 A1 | 3/2010 | Hart et al. |
| 2010/0075274 A1 | 3/2010 | Klett |
| 2010/0217567 A1 | 8/2010 | Marshall |
| 2010/0286568 A1* | 11/2010 | Xia ....................... A61B 5/1114 600/587 |
| 2010/0304325 A1 | 12/2010 | Fletcher |
| 2011/0027745 A1 | 2/2011 | Evenson |
| 2011/0053110 A1 | 3/2011 | Bando et al. |
| 2011/0066267 A1 | 3/2011 | Schmitt |
| 2011/0070562 A1 | 3/2011 | O'Brien et al. |
| 2012/0123577 A1 | 5/2012 | Chapoulaud et al. |
| 2012/0244487 A1 | 9/2012 | Tamburrino et al. |
| 2013/0130195 A1 | 5/2013 | Evenson |

* cited by examiner

DIGITAL FACE BOW SYSTEM AND METHOD

RELATED APPLICATIONS

This application is a non-provisional utility application of co-pending U.S. provisional patent application Ser. No. 61/862,281, filed Aug. 5, 2013, of Hansen, entitled "DIGITAL FACE BOW SYSTEM AND METHOD," which is incorporated herein by this reference.

TECHNICAL FIELD

The present invention relates to a digital dental apparatus and method for capturing a patient's dento-facial characteristics by acquiring and registering data defining the tilt or slant of the incisal and/or occlusal planes of a patient's maxillary teeth and/or arch in three planes of space in relation to the cranium, head and/or face.

BACKGROUND

Diagnostic information gathered early on from a patient is vitally important to the ultimate outcome of orthodontic and orthognathic procedures, treating conditions such as malalignment and jaw disorders, and in making dental prostheses and restorations. Indirect restorations, such as crowns, are typically fabricated outside of the patient's mouth. Usually an initial process step, such as making an impression of the patient's maxillary arch is necessary to make a maxillary model. If the maxillary model is not properly oriented to the patient's face at the time the diagnostic information is gathered, then a technician cannot design the teeth with the patient's face/smile in mind. If the existing maxillary teeth alone are used and the maxilla is canted or the teeth offset (i.e. with respect to the face/cranium) the quality of any resulting restoration may be adversely compromised.

Presently available face bow devices are used to analyze a patient's occlusion with reference to their cranium, head and/or face from both an esthetic and functional point of view. The objective is to allow dentists to replicate the orientation of the patient's teeth with reference to their cranium, head and/or face in three planes on an articulator.

There are many face bow systems available, but they have many drawbacks as they are complex, time consuming, and uncomfortable for the patient. Further, they are costly to use and frustrating for most dental clinicians to work with. One such system, called the dento-facial analyzer, simplified the face bow process significantly. However, it features a bite fork with gripping wings that are difficult to manipulate in three dimensions. Such manipulation is often done while dental impression or bite registration material is setting while being held in the patient's mouth, adding further difficulty and discomfort to the process.

As a result, dentists often avoid using face bows because they are awkward to use by the dentist, unpleasant for the patient and prone to error. At the same time it is often essential in order to properly predict functional and esthetic outcomes. Past devices have been designed to use certain facial landmarks to determine bite plane orientation, (i.e. pupillary eye line (horizontal reference plane), tip of the nose (sagittal mid-plane), Frankfort-horizontal, etc.) Unfortunately, both such hard and soft tissue landmarks are inherently asymmetrical and do not reflect the true relationship of the facial features to the jaw. Moreover, if only those landmarks are utilized in determining the orientation of the desired occlusal or incisal plane, numerous esthetic and functional problems, including an undesirable occlusal or incisal plane, a slanted maxillary mid-line and gingival line may result. While landmarks are important, they should be treated as guidelines. It is believed that all those analog devices can confuse the ability to assess the symmetry of the face.

In an advance over known face bow systems, the present invention minimizes the amount of extra-oral mechanical-analog equipment, allowing the clinician and the patient to orient the patient's head into a desirably natural and, consequently, level position, with reference to both vertical and horizontal planes, at which point the digital orientation of the maxillary incisal and occlusal planes can be captured with a push of a button. In other cases it is not even necessary to move the patient's head. Further, the present invention will integrate quite easily into existing impression procedures which are used ubiquitously. In addition to every study model receiving a name and accompanying data, the dental professional will also receive a set of digital coordinates for use should the dentist need to relate the orientation of dentition to the face or cranium on an articulator. This information can accompany the models to a dental lab. There is no need for unwieldy analog face bows to accompany models. Further, the presently disclosed method does not require manipulation of external analog devices while impression material is setting. Virtually all analog manipulation is achieved indirectly (i.e. patient need not be present) with a mounting platform that can quickly replicate the maxillary incisal and occlusal planes in 3 dimensions and permit study casts to be transferred to any articulator the dentist or dental lab technician may be using. Alternatively, the digital information can be used with other digital systems and processes such as CAD CAM, digital impression techniques and 3D printing.

BRIEF SUMMARY OF THE DISCLOSURE

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a digital face bow system is disclosed for capturing a patient's dento-facial characteristics by acquiring and registering data defining the tilt or slant of the occlusal or incisal plane of a patient's teeth in three planes of space in relation to the cranium, head and/or face. The system includes a substrate adapted to support bite registration or dental impression material, and a digital multiple axis inclinometer coupled to the substrate for registering the orientation of the occlusal or incisal plane, whereby the midline of the patient's horizontal-facial plane is registered.

In another aspect, a digital face bow also comprises an adjustable mounting platform adapted to receive the substrate and replicate the inclination registered by a digital inclinometer.

In another aspect, the digital multiple axis inclinometer comprises a microsensor accelerometer.

In another aspect, the microsensor accelerometer comprises a wide range dual axis angle measurement sensor.

In another aspect, the index tray comprises an alignment element having a mid-sagittal indicator.

In another aspect, the substrate comprises a device selected from the group consisting of an index tray, an impression tray and a dental jig.

In yet another aspect, the substrate comprises an index tray including an alignment element having a substantially planar wall running linearly along or substantially parallel to an incisal line and protruding from and substantially perpendicular to the top surface of the index tray; and a mid-sagittal indicator substantially perpendicular to the top surface of the index tray and located at the mid-point of the index tray.

In another aspect, the index tray includes an inclinometer mounting surface for mounting the inclinometer.

In a further aspect, a system for acquiring and transmitting digital face bow data is provided including a digital index assembly including an inclinometer mounted thereon. A processor includes a display, where the processor is adapted to receive face bow data transmitted from the inclinometer; and a switch is coupled to the processor for capturing face bow data when activated.

In another aspect, the switch comprises a foot pedal, or push button switch.

In another aspect, the face bow data is transmitted directly by wire or wirelessly to the processor.

In another aspect, the face bow data is transmitted to a storage media or to the Internet.

In another aspect, a method for using a digital face bow system is disclosed including applying impression material to a digital index assembly. The digital index assembly is placed in a patient's mouth. A selected medial point is noted with reference to the patient's face or landmarks, and selected face bow data is registered.

In another aspect, the digital index assembly is removed from the patient's mouth and placed on an adjustable platform.

In another aspect, the method includes replicating the registered face bow data by manipulating the adjustable platform to substantially match the registered face bow data.

In another aspect, the method includes mounting the digital index assembly and a maxillary cast on an adjustable platform.

In another aspect, the method includes applying a mounting medium applied to affix the maxillary cast in the articulator.

In another aspect, the method includes mounting medium comprising stone slurry or mounting plaster.

In another aspect, the method includes noting a selected medial point with reference to the patient's face or landmarks by aligning a sagittal indicator with the patient's facial-sagittal midline.

In another aspect, the method includes noting a selected medial point with reference to the patient's face or landmarks by applying a reference mark to a reference area.

In another aspect, a method for analyze a patient's occlusion with reference to their cranium, head and/or face is provided comprising:

applying impression material to a digital index assembly including a first inclinometer;

placing the digital index assembly in a patient's mouth;

obtaining a bite registration or impression of the maxillary arch or dentition;

aligning a second inclinometer externally with the patient's cranium; and recording the tilt of the occlusal and/or incisal plane of the patient's teeth in three planes of space in relation to the cranium or head with both the first inclinometer and the second inclinometer.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE PREFERRED EMBODIMENTS

The following disclosure describes several embodiments for a digital face bow system. Several features of methods and systems in accordance with example embodiments are set forth and described in the Figures. It will be appreciated that methods and systems in accordance with other example embodiments can include additional procedures or features different than those shown in the Figures. Example embodiments are described herein with respect to a digital face bow integrated into a restoration procedure. However, it will be understood that these examples are for the purpose of illustrating the principles, and that the invention is not so limited. Additionally, methods and systems in accordance with several example embodiments may not include all of the features shown in the Figures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally, as used herein, the following terms have the following meanings when used within the context of dentistry:

Cloud computing is understood herein as to describe a variety of different types of computing concepts that involve a large number of computers that are connected through a real-time communication network (typically the Internet). For example, storage of data in a "cloud" means storage in an Internet server, for example, for later retrieval or archival purposes.

As used in this specification, the term "incisal line" is meant a substantially straight line defined by an idealized alignment of a set of human incisors across the front of the patient's mouth.

As used herein, "plurality" is understood to mean more than one. For example, a plurality refers to at least two, three, four, five, ten, 25, 50, 75, 100, or more.

As used in this specification, the terms "processor" and "computer processor" encompass a personal computer, a tablet computer, a smart phone, a microcontroller, a microprocessor, a field programmable object array (FPOA), a digital signal processor (DSP), an application-specific integrated circuit (ASIC), a field programmable gate array (FPGA), a programmable logic array (PLA), or any other digital processing engine, device or equivalent capable of executing software code including related memory devices, transmission devices, pointing devices, input/output devices, displays and equivalents.

In brief, in operation, the digital face bow system disclosed herein has an index or impression tray that captures the midline of the patient horizontal-facial plane which is registered. The midline can be captured in a number of ways:

1. Drawing or noting a reference point at the most medial point;
2. Orienting the delivery handle at the most medial point of the face (for example, using a removable handle);
3. Locating a dot or vertical line to measure the most medial point of the face (e.g. use a different color or modified topography on index or impression tray) (Note that a dot may be preferable as a drawn vertical line may end up being slanted.); or
4. Using a mechanical attachment to register a precise midpoint.

Bite registration material is used to provide an index for study casts (digital impression/models). With the patient's cranium or head facing forward, in a balanced posture with reference to all three planes, coronal, sagittal, horizontal or transverse the inclination of the patient's bite is registered in the coronal plane and sagittal plane with a digital multiple axis inclinometer accelerometer. The transverse orientation is registered on a digital index assembly by, for example, creating a reference mark at the most medial point. A more detailed description follows herein below.

Figure 1:
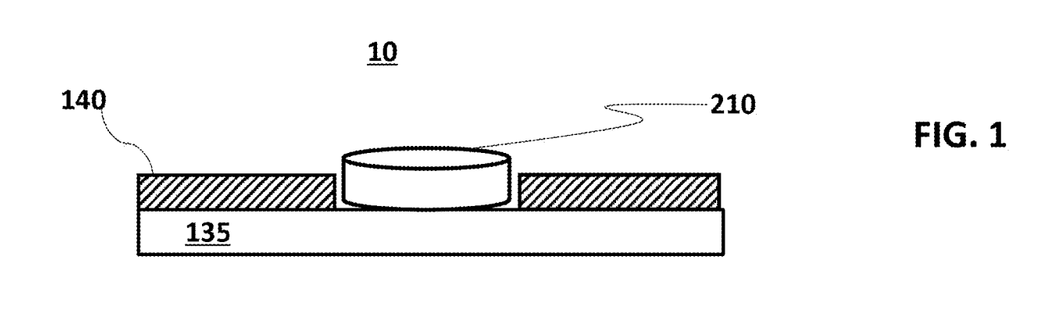
FIG. 1 schematically shows one example of a digital index assembly.

Referring now to FIG. 1 one example of a digital index assembly is schematically shown. A digital index assembly 10 includes a substrate 135 on which is mounted a digital tilt sensor, such as a digital multiple axis inclinometer 210. In order to obtain an index of the patient's occlusion with reference to their cranium, head and/or face an indexing material 140 may advantageously be applied to the substrate if the device is to be used intraorally. Indexing materials may comprise any suitable material for registering an impression of a bite. Tilt sensors and inclinometers generate an artificial horizon and measure angular tilt with respect to this horizon. Thus, it is desirable in the case a seated or standing patient to have the patient's head level with respect to the horizon in order to obtain more accurate readings with a single digital tilt sensor. Examples of these elements are described hereinbelow with reference to more specific examples. The specific examples are by way of illustration only and the invention is not to be construed as limited by the examples.

Figure 1A:
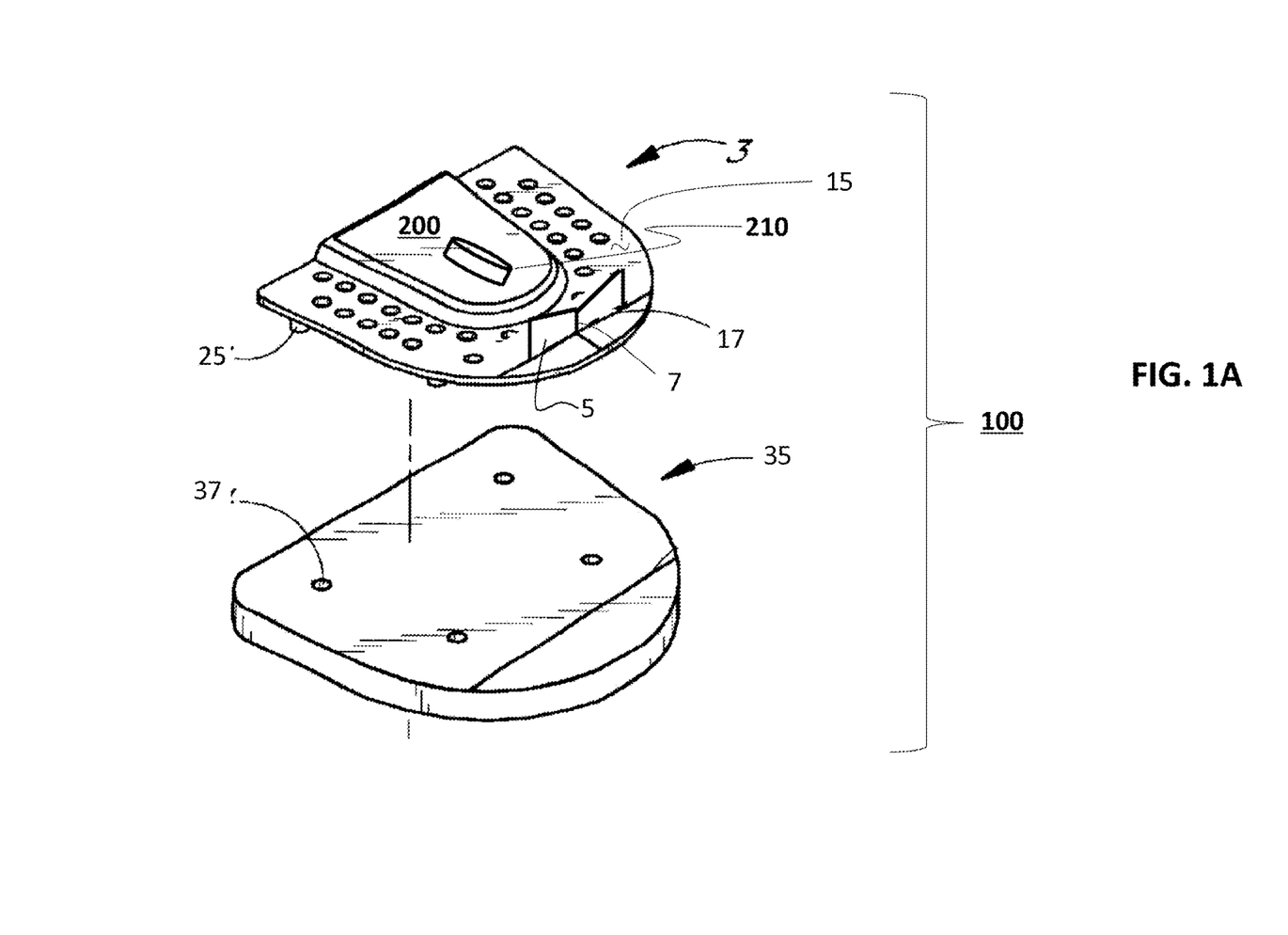
FIG. 1A schematically shows one example of an intraoral digital index assembly element in alignment with an adjustable mounting platform.

Referring now to FIG. 1A one example of an intraoral digital index assembly element in alignment with an adjustable mounting platform is schematically shown. An intraoral digital index assembly system 100 includes a substrate, such as an index tray 3. The index tray 3 may optionally include an alignment element 5 including a mid-sagittal indicator 7 on a top surface 15. In one embodiment the alignment element 5 may be a substantially planar wall running linearly along or substantially parallel to an incisal line and protruding from and substantially perpendicular to the top surface of the index tray 3. The mid-sagittal indicator 7 is also substantially perpendicular to the top surface of the index tray 3 and is located at the mid-point of the index tray 3. The index tray 3 may further include an inclinometer mounting surface 200 on which is mounted an inclinometer 210.

In one embodiment, the index tray may include a scribed line 17 representing an incisal line reference which is bisected by the indicator 7. The index tray 3 preferably includes a plurality of locating keys 25 such as protruding pins or the like. The index tray 3 is configured to mount on a mounting surface 35 having a plurality of mounting holes 37 located to mate to the plurality of locating keys 25 in order to orient the index tray 3 onto the mounting surface 35.

It will be understood by those skilled in the art having the benefit of this disclosure that the above-described elements may be of any convenient shape, size or configuration and that the invention is not so limited. For example, it may not be necessary to include an incisal reference line or a mid-sagittal indicator as long as a desirable medial point may be noted with reference to the patient's face. As a further example, the locating keys may be of any convenient style.

Figure 2:
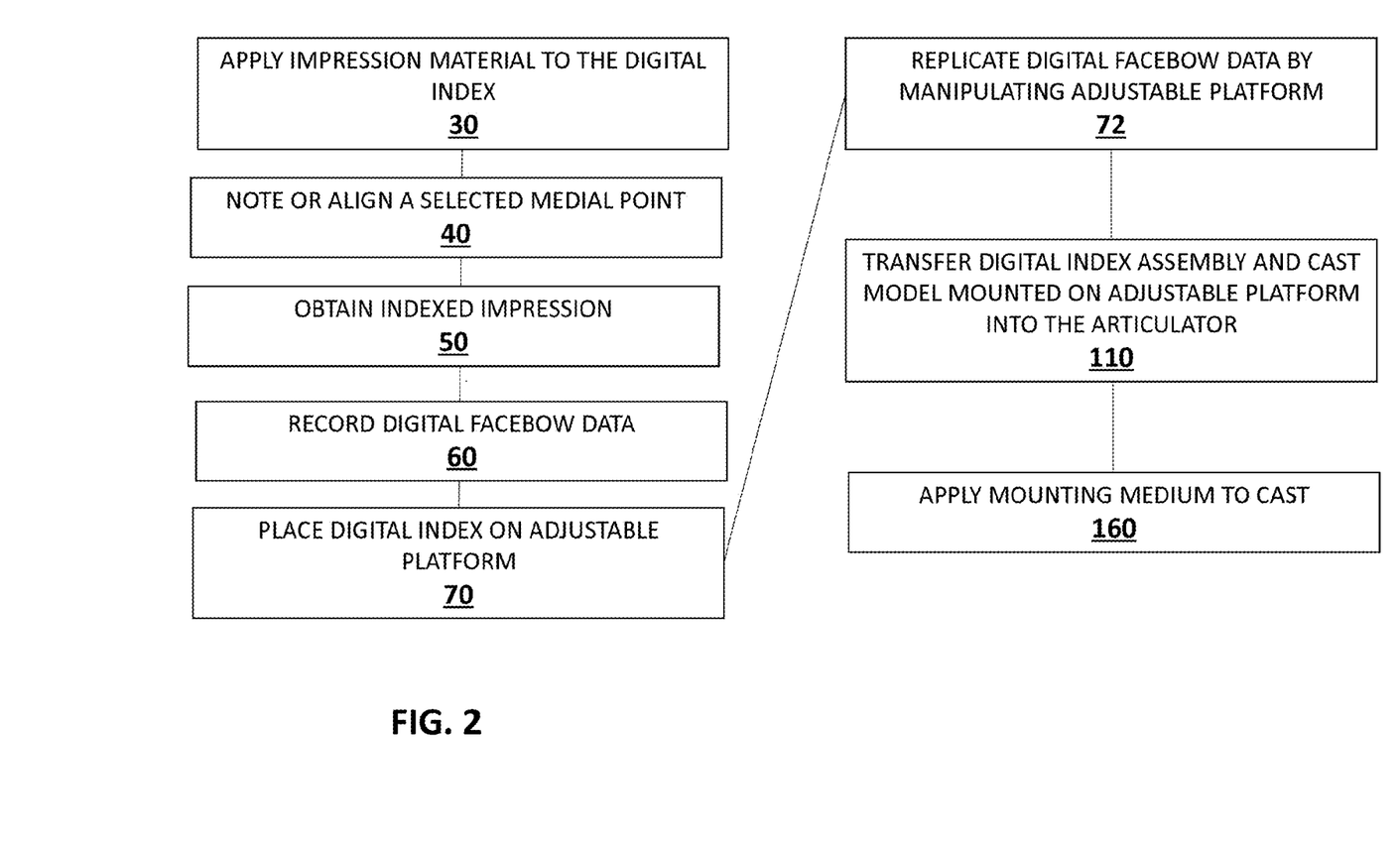
FIG. 2 schematically shows a flow diagram of one example of a method for using a digital face bow system.

Referring now to FIG. 2, a flow diagram of one example of a method for using a digital face bow system is schematically shown. In one example, the process begins with the step of applying impression material to the digital index assembly 30. The digital index assembly is placed in the patient's mouth and the sagittal indicator is aligned with the facial-sagittal midline 40 as visually or otherwise determined by the operator inserting the digital index assembly. Alternatively the most medial point may be noted with reference to the patient's face or landmarks such as on the dentition, the alveolus and/or the digital index assembly.

Once the data is registered the digital index assembly can be removed from the patient's mouth and be placed on an adjustable platform 70. From this point on it is not necessary to have the patient present and the remaining steps can be performed remotely by a dental laboratory, for example. Digital face bow data is replicated 72 by manipulating the adjustable platform as described further herein. The acquired digital face bow data, together with the indexed impression now quickly and reliably provides the required dento-facial relationships needed for diagnosis and treatment.

The digital index assembly and a previously made maxillary cast model from the patient may then be positioned on an adjustable platform and transferred into an articulator 110. A mounting medium such as stone slurry or mounting plaster is applied to affix the maxillary cast in the articulator 160.

Figure 3:
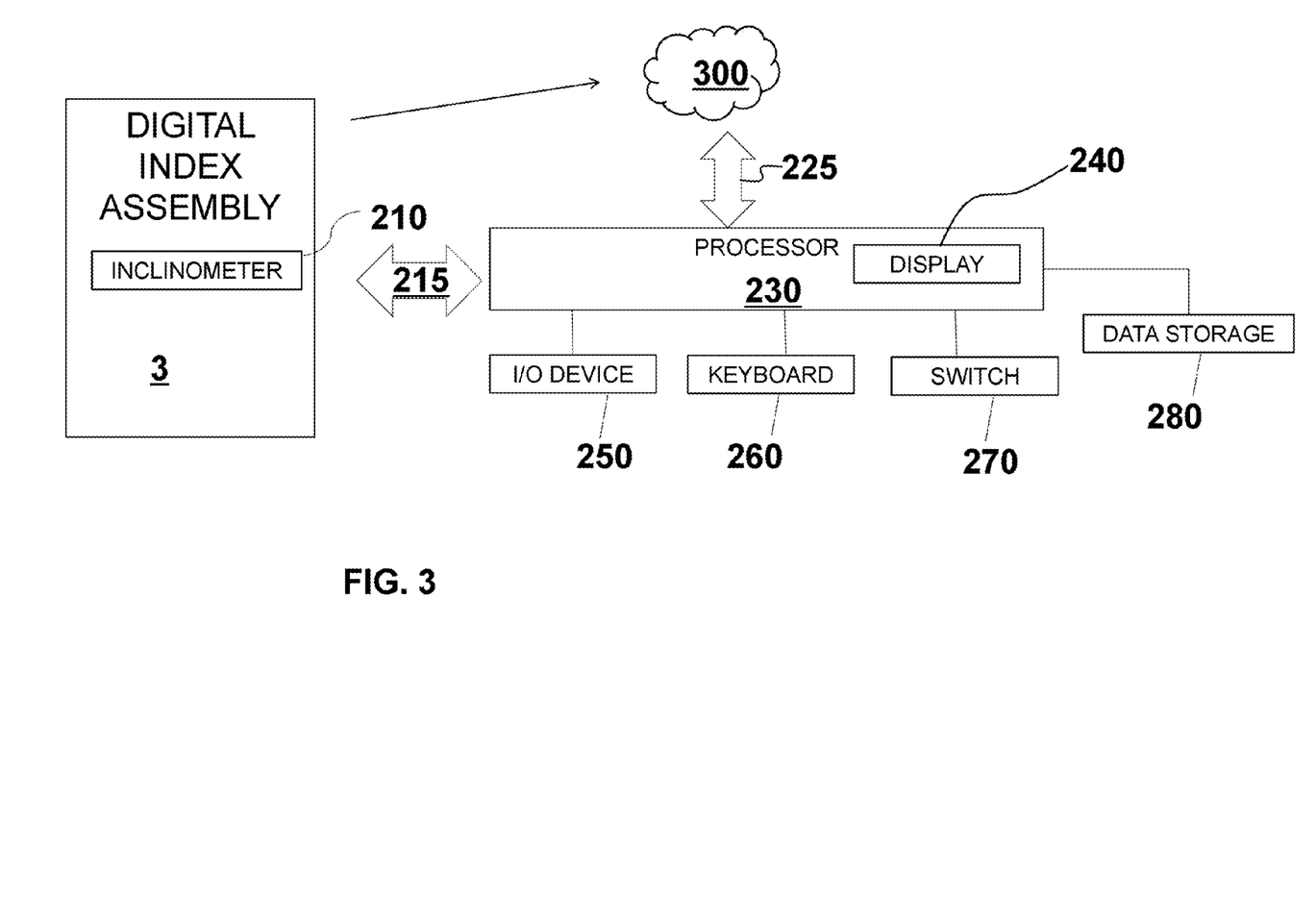
FIG. 3 schematically shows one example of a system for acquiring and transmitting digital face bow data.

Referring now to FIG. 3, one example of a system for acquiring and transmitting digital face bow data is schematically shown. A digital face bow system including a digital index assembly 3 having an inclinometer 210 mounted thereon. A processor 230 including a display 240 is adapted to receive data 215 from the inclinometer 210. The processor may preferably include or be coupled to an input/output device 250, such as, for example a computer mouse or pad, a keyboard 260, and a data storage medium 280. A switch 270 may be coupled to the processor for the purpose of, for example, capturing selected face bow data at desired times or when a patient is in a favorable position as observed by an operator. The switch may be, for example a foot pedal, push button switch or the like which is activated by an operator to capture useful face bow data. The processor advantageously can include a software application, designed according to standard software techniques, for recording, organizing, and storing data representing the digital orientation of the bite plane.

Note that the data 225 may be transmitted by any conventional means such as, for example, directly by wire or wirelessly to the processor 230. If desired or if the processor is at a remote location, the data may be transmitted to any available storage media or to the Internet as by the use of cloud technology 300.

In one example, during data collection, a dental professional may have the patient move into a number of positions and record selected face bow data at a number of selected positions - including repeated movements for some or all positions. In this way, selected measurements can be collected and statistically processed to produce an averaged data set in order to reduce the possibility of erroneous data capture. The data set can be processed off-line or in real time depending on the application of the data set.

Figure 4:
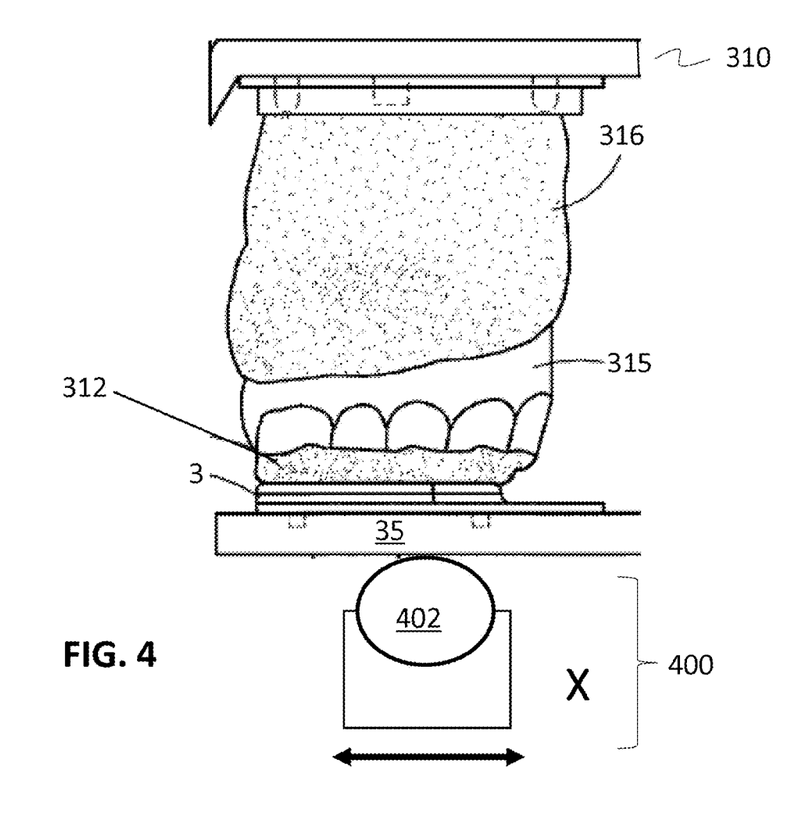
FIG. 4 schematically shows one example of a maxillary cast oriented on a digital index assembly mounted in an articulator having an adjustable mounting platform.

Referring now to FIG. 4, one example of a maxillary cast oriented on a digital index assembly mounted in an articulator having an adjustable mounting platform is schematically shown. Since dental articulators are well known, only the parts of the articulator helpful to the description are being shown in order to simplify the drawing. The system further includes an adjustable mounting platform that can replicate the inclination registered by digital inclinometer and receive the index or impression trays, allowing study models to be mounted in the proper orientation on a dental articulator.

A section of an articulator's upper support arm 310 is shown in a horizontal orientation. The patient's maxillary cast 315 is positioned on the impressions that are in the bite registration or dental impression material 312 adhered to the digital index assembly 3, and a mounting medium such as plaster or stone slurry material 316 is utilized to connect the maxillary cast to the upper frame of the (partially shown) dental articulator. The mounting surface 35 is coupled to an adjustable mounting platform 400 including, for example, a tilting mechanism 402, such as a ball bearing or the like.

While not seen in this drawing, the inclinometer may advantageously be activated to provide readouts to an operator during the orientation process on the articulator. The readouts may be displayed on a processor display such as, for example, a personal computer, a smart phone, a computer tablet or the like. The articulator operator can use, for example, the mid-sagittal indicator 7 (shown above with reference to FIG. 1A), or the noted medial point and the digital face bow data as displayed on the processor, smart phone, computer tablet or other suitable device, to orient the maxillary cast prior to applying the mounting medium for final placement within the articulator. In this way the dentofacial relationships are preserved. It will be understood that, once the initial face bow data is acquired from the patient, the subsequent measurements and processes described herein can be done in any location or laboratory.

Note that in additional to tilting functions as provided by the tilting mechanism, the adjustable mounting platform is also adapted to move inwardly and outwardly with respect to a direction perpendicular to the drawing sheet as indicated by the large "X". The adjustable mounting platform is also capable of moving from side to side as indicated by the double-headed arrow at the bottom of the base. In summary, in one useful embodiment the adjustable mounting platform is designed using standard engineering principles to be moved forward, backward and side to side with respect to the stationary articulator as might be needed for a more specific location with respect to the condylar hinge axis.

Figure 5:
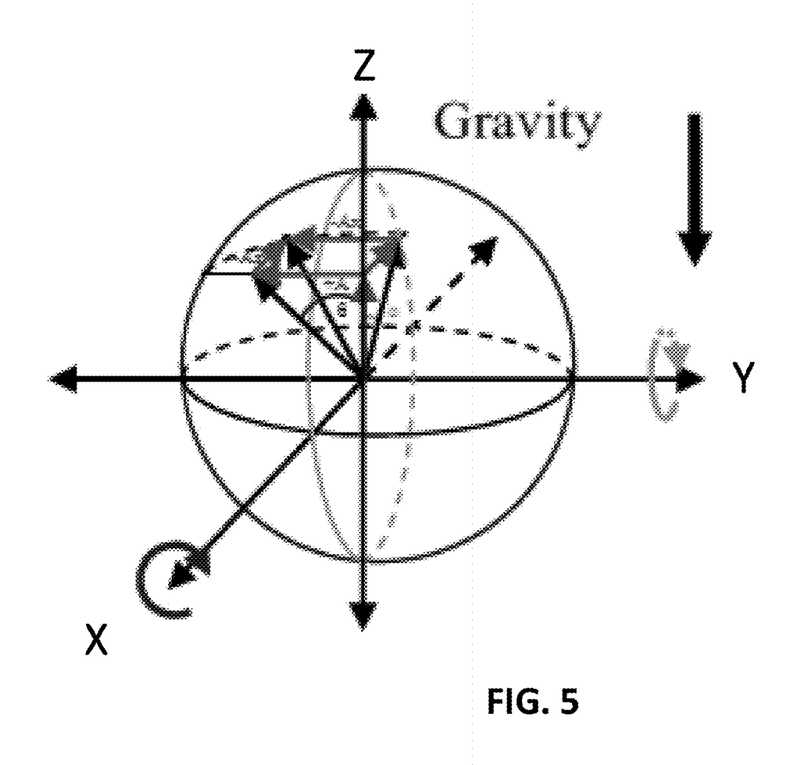
FIG. 5 schematically shows one example of a range of angles capable of being sensed by an inclinometer mounted in the digital index assembly.

Referring now to FIG. 5, one example of a range of angles capable of being sensed by an inclinometer mounted in the digital index assembly is schematically shown using a Cartesian coordinate system. In one useful embodiment of the presently disclosed digital face bow system, the inclinometer may comprise an accelerometer system. One example of a commercially available model of a microsensor inclinometer is the "MEMS Inclinometer—Wide Range—SQ-SI2X-360DA," made according to known principles by SignalQuest, Inc. of Lebanon, N.H. 03766 USA. The MEMS inclinometer performs calibrated angle measurement with analog voltage and digital serial outputs and features the following characteristics:

Functions

Wide range 360°×180° dual axis angle measurement.

Features

±1° accuracy—differential.

0.1° resolution—digital serial output.

2° resolution—analog output.

Low temperature drift.

Factory calibrated angle output.

High reliability solid-state MEMS.

Digital filtering for stable measurement.

Direct PC interface cable.

As shown in FIG. 5, the dual angle capabilities include angular sensing in the X and Y axes as well as pitch and roll rotational measurements. It will be understood that the invention is not limited to a dual angle inclinometer and other inertial sensors may be employed including 3 axis position sensors or the like.

Figure 6:
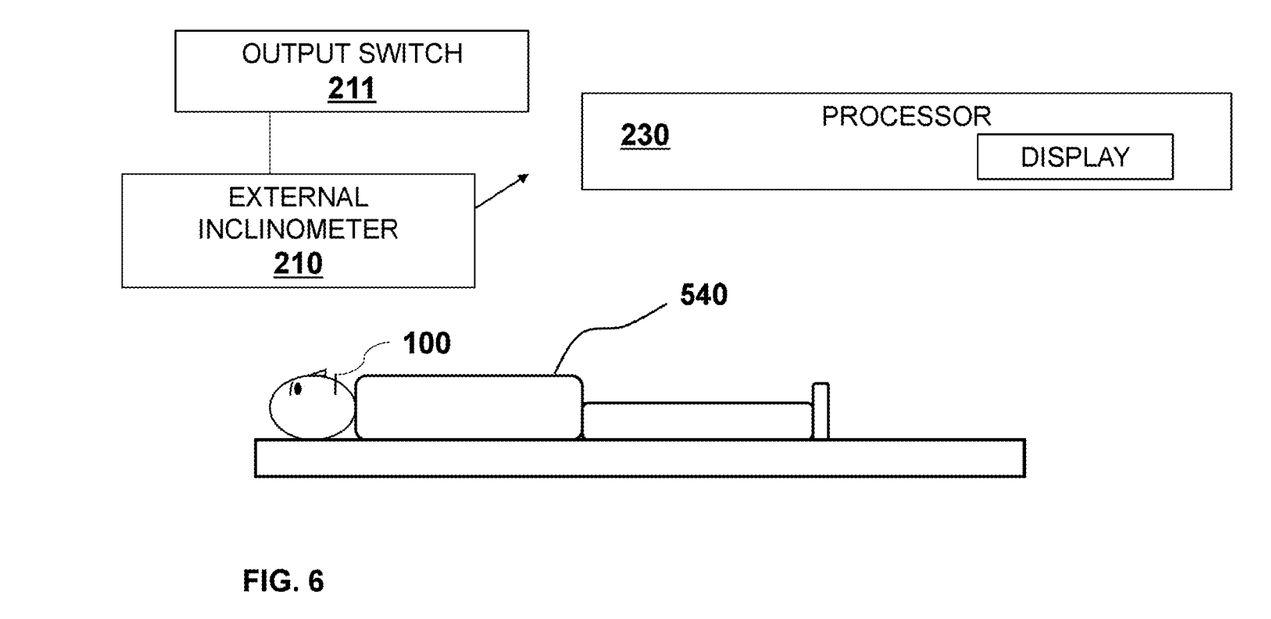
FIG. 6 schematically shows one example of a dual inclinometer system used in cases where establishing a reference to a horizon is difficult.

Referring now to FIG. 6 one example of a dual inclinometer system used in cases where establishing a reference to the horizon is difficult is schematically shown. There may be circumstances in which the patient cannot achieve a balanced posture with respect to the horizon. For example, the patient 540 may be sedated or have a medical condition affecting their posture. In these situations the measurement of the occlusal and/or incisal plane with reference to the horizon is not possible unless the cranium can be manipulated into the desired position. Alternatively, a second external facebow multiple axis inclinometer device 210 may be utilized in addition to the intraoral index inclinometer device 100. In one example incorporating a handheld device, the operator can position the handheld external device 210 around the patient's cranium aligning it harmoniously to the patient's innate 3 planes of space.

While the patient is wearing the intraoral index inclinometer device 100, the reading of both the intraoral and external inclinometers can be obtained, as by activating a switch 211 controlling outputs of both devices simultaneously transmitting data to the processor 230. Together the intraoral and external inclinometer readings can be used to determine the net tilt or slant of the occlusal and/or incisal plane of the patient's teeth in three planes of space in relation to the cranium or head. The net tilt and the net slant of the occlusal and/or incisal plane can be determined by calculating the differential between the corresponding measurements of the intraoral and external digital sensor measurements. Thus, establishment of a reference to a horizon is not required. The net angular spatial data simultaneously achieved with both an intraoral and extraoral inclinometer can be similarly transferred to an articulator as in the method described above. Note that in all cases the inclinometer and control switch may communicate electronically by wires or wirelessly or through an internet or intranet network.

The invention has been described herein in considerable detail in order to comply with the Patent Statutes and to provide those skilled in the art with the information needed to apply the novel principles of the present invention, and to construct and use such exemplary and specialized components as are required.

However, it is to be understood that the invention may be carried out by different equipment, and devices, and that various modifications, both as to the equipment details and operating procedures, may be accomplished without departing from the true spirit and scope of the present invention.

What is claimed is:

1. A digital face bow system for capturing a patient's dento-facial characteristics by acquiring and registering data defining the tilt or slant of the occlusal or incisal plane of a patient's teeth in three planes of space in relation to the cranium, head and/or face, the system comprising:
    a substrate adapted to support bite registration or dental impression material;
    a digital multiple axis inclinometer coupled to the substrate for registering the orientation of the occlusal or incisal plane, wherein the substrate comprises an index tray including an alignment element having a substantially planar wall running linearly along or substantially parallel to an incisal line and protruding from and substantially perpendicular to the top surface of the index tray, and a mid-sagittal indicator substantially perpendicular to the top surface of the index tray and located at the mid-point of the index tray; and
    wherein the index tray also includes an inclinometer mounting surface for mounting the digital multiple axis inclinometer.

2. The digital face bow system of claim 1 also comprising an adjustable mounting platform adapted to receive the substrate and replicate the orientation registered by the digital multiple axis inclinometer.

3. The digital face bow system of claim 1 wherein the digital multiple axis inclinometer comprises a microsensor accelerometer.

4. The digital face bow system of claim 3 wherein the microsensor accelerometer comprises a wide range dual axis angle measurement sensor.

5. The digital face bow system of claim 3 wherein the index tray comprises an alignment element having a mid-sagittal indicator.

6. The digital face bow system of claim 1 further comprising:
    a processor including a display, where the processor is adapted to receive face bow data transmitted from the the digital multiple axis inclinometer; and
    a switch coupled to the processor for capturing face bow data transmitted from the inclinometer when activated.

7. The system of claim 6 wherein the switch comprises a foot pedal, or push button switch.

8. The system of claim 6 wherein the face bow data transmitted from the the digital multiple axis inclinometer is transmitted directly by wire or wirelessly to the processor.

9. The system of claim 6 wherein face bow data is transmitted to a storage media or to the Internet.

10. A method for using a digital face bow system comprises:
    applying impression material to a digital index assembly;
    placing the digital index assembly with the applied impression material in a patient's mouth;
    using the digital index assembly with the applied impression material to obtain a bite registration or impression of the maxillary arch or dentition;
    noting a selected medial point with reference to the patient's face or landmarks;
    recording selected face bow data using a first inclinometer; and
    removing the digital index assembly from the patient's mouth and placing it on an adjustable platform.

11. The method of claim 10 further comprising replicating the registered face bow data by manipulating the adjustable platform to substantially match the registered face bow data.

12. The method of claim 11 further comprising mounting the digital index assembly and a maxillary cast on the adjustable platform.

13. The method of claim 12 further including applying a mounting medium applied to affix the maxillary cast in the adjustable platform.

14. The method of claim 13 wherein the act of applying a mounting medium comprises stone slurry or mounting plaster.

15. The method of claim 10 wherein the act of noting a selected medial point with reference to the patient's face or landmarks comprises aligning a sagittal indicator with the patient's facial-sagittal midline.

16. The method of claim 10 wherein the act of noting a selected medial point with reference to the patient's face or landmarks comprises applying a reference mark to a reference area.

17. The method of claim 10 wherein the act of recording further comprises:
    aligning a second inclinometer externally with the patient's cranium, head and/or face; and
    recording the tilt of the occlusal and/or incisal plane of the patient's teeth in three planes of space in relation to the cranium or head with both the first inclinometer and the second inclinometer.

* * * * *